(12) United States Patent
Eden

(10) Patent No.: US 6,797,149 B2
(45) Date of Patent: Sep. 28, 2004

(54) APPARATUS AND METHOD FOR ELECTROCHEMICAL DETECTION AND CONTROL OF INORGANIC SCALE

(75) Inventor: David A. Eden, Houston, TX (US)

(73) Assignee: Intercorr Holdings, Ltd., Aberdeen (GB)

( * ) Notice: Subject to any disclaimer, the term of this patent is extended or adjusted under 35 U.S.C. 154(b) by 308 days.

(21) Appl. No.: 10/114,512

(22) Filed: Apr. 2, 2002

(65) Prior Publication Data

US 2003/0183536 A1 Oct. 2, 2003

(51) Int. Cl.$^7$ .................. G01N 27/403; G01N 27/42
(52) U.S. Cl. .................. 205/775.5; 205/777; 204/404; 204/409
(58) Field of Search ................ 205/775.5, 776.5, 205/777; 204/404, 409, 411

(56) References Cited

U.S. PATENT DOCUMENTS

| | | | | |
|---|---|---|---|---|
| 4,426,618 A | * | 1/1984 | Ronchetti et al. | 324/700 |
| 4,533,457 A | * | 8/1985 | Watanabe | 204/411 |
| 4,840,719 A | * | 6/1989 | Jasinski | 204/404 |
| 6,089,576 A | * | 7/2000 | Hollenbaugh et al. | 277/650 |
| 6,228,943 B1 | * | 5/2001 | Morikawa et al. | 525/199 |

OTHER PUBLICATIONS

Several entries for Austentic Cr–Ni–Mo Stainless Steel (17–2–3; 316L/317L) from the online Corrosion Survey Database (COR–SUR) copyright 2002.*

* cited by examiner

Primary Examiner—Alex Noguerola
(74) Attorney, Agent, or Firm—Raymond R. Ferrera; Arnold & Ferrera, LLP

(57) ABSTRACT

An electrochemical scale detection and control system, for on-line detection and control of nucleation and growth of inorganic scales. The system comprises sensitive microprocessor controlled electrochemical monitoring instrumentation for detecting electrochemical changes which occur as a consequence of scale nucleation, growth and removal, with subsequent processing to provide means of controlling scale inhibitor additions. The device takes measurements continuously and provides uninterrupted output of the scaling tendency. A three-element measurement probe consisting of material having little propensity for corrosion in the scaling medium of interest is used as the scale sensor.

17 Claims, 7 Drawing Sheets

APPARATUS AND METHOD FOR ELECTROCHEMICAL DETECTION AND CONTROL OF INORGANIC SCALE

CROSS-REFERENCE TO RELATED APPLICATIONS

Not Applicable

STATEMENT REGARDING FEDERALLY SPONSORED DEVELOPMENT

Not Applicable

BACKGROUND OF THE INVENTION

1. Field of the Invention

The present invention is directed generally to an apparatus and method for detecting and controlling inorganic scale in commercial and industrial environments, and more particularly to an apparatus and method for obtaining and evaluating a variety of electrochemical response signals relating to scale nucleation and growth by means of a plurality of independent corrosion-resistant sensors operating in electrical communication with a microprocessor controlled electrochemical monitoring instrument.

2. Background of the Invention

Presently, establishment of electrochemical measurements, including electrochemical noise, polarization resistance, harmonic distortion analysis, and electrochemical impedance spectroscopy, involves a number of related devices and methods, the collective functions of which are essentially to define the charge transfer characteristics of various electrochemical oxidation and reduction processes occurring in association with the corrosion of metals. Such measurement techniques typically require considerable sensitivity regarding the nature of the metal/electrolyte interface characteristics being evaluated, and the various dynamic changes that may be occurring around the boundary interface.

For example, one previously known corrosion measurement technique involves the introduction of a sensor similar in composition to the material being corroded into a surrounding fluid stream, and then evaluating various Faradaic charge transfer characteristics related to the corrosion process by means of electrochemical comparison methods. Of principal interest in such evaluations is a determination of the material's loss rate due to corrosion.

In contrast, in process streams having a propensity to form inorganic scale, the metal interior surfaces of pipelines or vessels or the like provide energetically favorable nucleation sites for scale deposition. When scale deposition subsequently occurs around such nucleation sites, the characteristics of the surrounding metal/electrolyte interface are necessarily dynamically altered. As the scale thickens, the response of the metal/electrolyte interface is further altered. Thus, in such scale-favorable environments, it is inevitably the scaling behavior rather than the corrosion behavior that becomes primarily important in commercial and industrial environments.

Previous methods used for detecting the presence of scale nucleation and deposition have therefore generally been dependent on measuring one or more additional physical changes indicative of the scale's presence, such as changes in the heat transfer resistance, or in the resonant frequency of piezo crystal elements. Those of ordinary skill in the appropriate arts, however, will appreciate that such methods typically are relatively slow to detect the evolution of scale deposition, especially within the confines of certain industrial applications, and also frequently employ sensors prone to mechanical damage due to the corrosive properties of the fluid medium.

As a result of such mechanical damage, most sensors cannot be continuously used, due to the inevitable decline in the devices' structural integrity and measurement sensitivity, and thus repetitive testing or calibration of the sensors is often required. Such methods and their associated devices often further suffer from the fact that an entire processing system or, at minimum, constituent components of a system, must be taken off-line in order for the testing and calibration to be carried out by technicians.

3. Object of the Invention

In view of the foregoing, a primary object of the present invention is to provide an apparatus and method for inexpensively obtaining and evaluating a variety of reliable electrochemical response signals relating to scale nucleation and growth by means of a plurality of independent corrosion-resistant sensors operating in electrical communication with a microprocessor controlled instrument, so that appropriate processes for controlling and inhibiting the scale can be initiated while a system employing the apparatus remains on-line.

BRIEF SUMMARY OF THE INVENTION

According to a presently preferred embodiment of the invention, an apparatus suitable for detecting initiation of electrochemical scale nucleation and the associated growth of scaling deposits is provided, wherein a sensor comprising an array of three metallic electrodes is disposed within fluids in which conditions favorable to scale nucleation and deposition are believed to exist. A presently preferred method of practicing the invention is also provided wherein one or more of a plurality of electrochemical measurement techniques are applied to the apparatus' electrodes, for example, electrochemical noise, linear polarization resistance, harmonic distortion analysis, intermodulation distortion analysis, electrochemical impedance, and/or solution resistance. Associated electrochemical characteristics of the sensor/fluid interface are then monitored continuously during scaling, and can be used to identify subsequent initiation of additional nucleation and deposition. The apparatus may further be used to control the addition of scale inhibitor formulations useful in the mitigation of scale formation, and to monitor the progress of scale removal in a controlled and predictable manner while the fluid transport system or the like remains on-line.

DETAILED DESCRIPTION OF THE INVENTION

Figure 1:
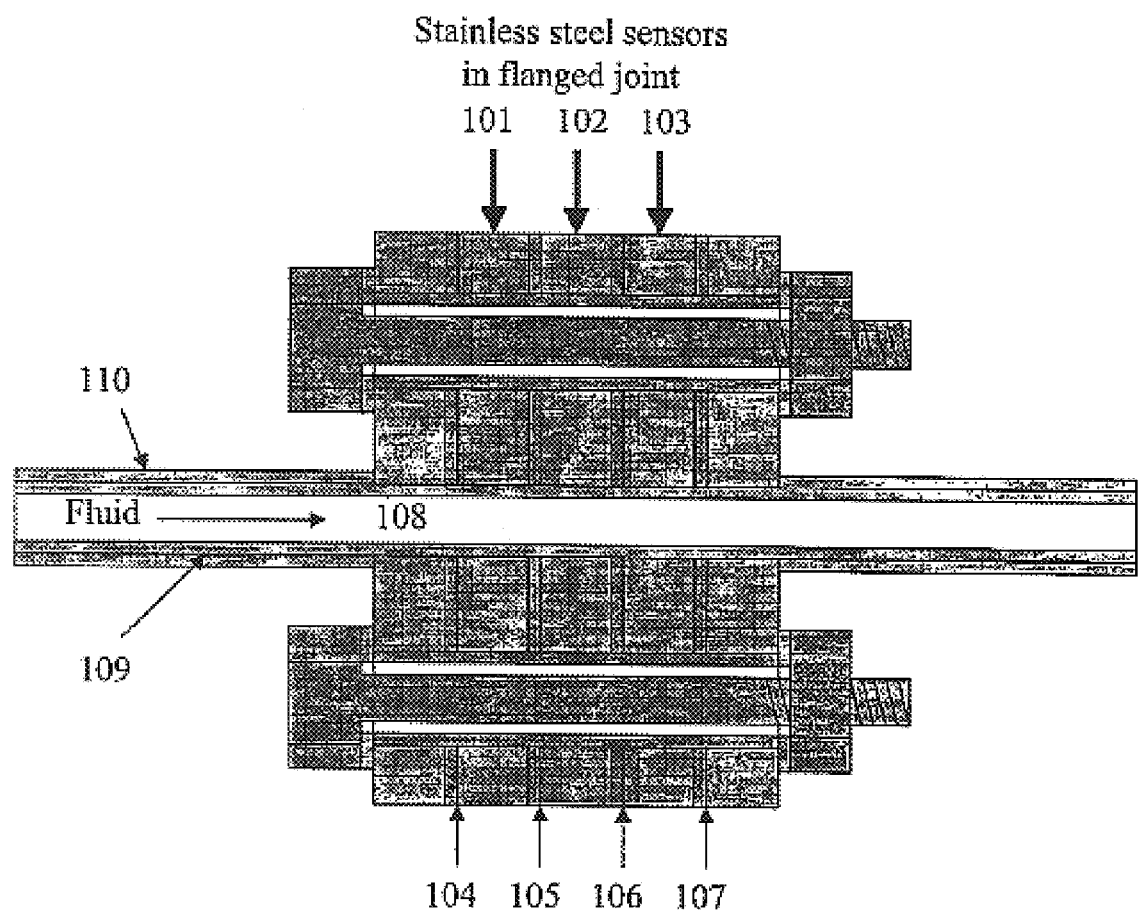
FIG. 1 is a schematic drawing of a three-sensor array housed within a flanged sensor body according to one aspect of the present invention.

Referring now to FIG. 1, an apparatus for electrochemical detection and control of inorganic scale is provided having a sensor array 101, 102 and 103, wherein said apparatus is suitable for use either directly within a fluid flow line or in a side stream loop. As shown, sensors 101–103 are essentially electrically isolated sections of electrochemical sensor material, for example stainless steel, housed within a flanged sensor body, and in discrete electrical communication with an electrochemical monitoring device (not shown).

Electrical isolation between sensors 101–103 is maintained by a plurality of gaskets 104–107, which those of ordinary skill in the art will appreciate may be formed from any suitable dielectric insulating material, for example, PTFE, PVDF or another similar material. The flanged sensor body is disposed either around or alongside the fluid flow stream via flow tube 110. Fluid 108 flows through flow tube 110 as it is produced by the fluid transport system or the like (not shown), and electrochemical scale 109 is formed on the inside of the tube 110 and on sensors 101–103.

Figure 2:
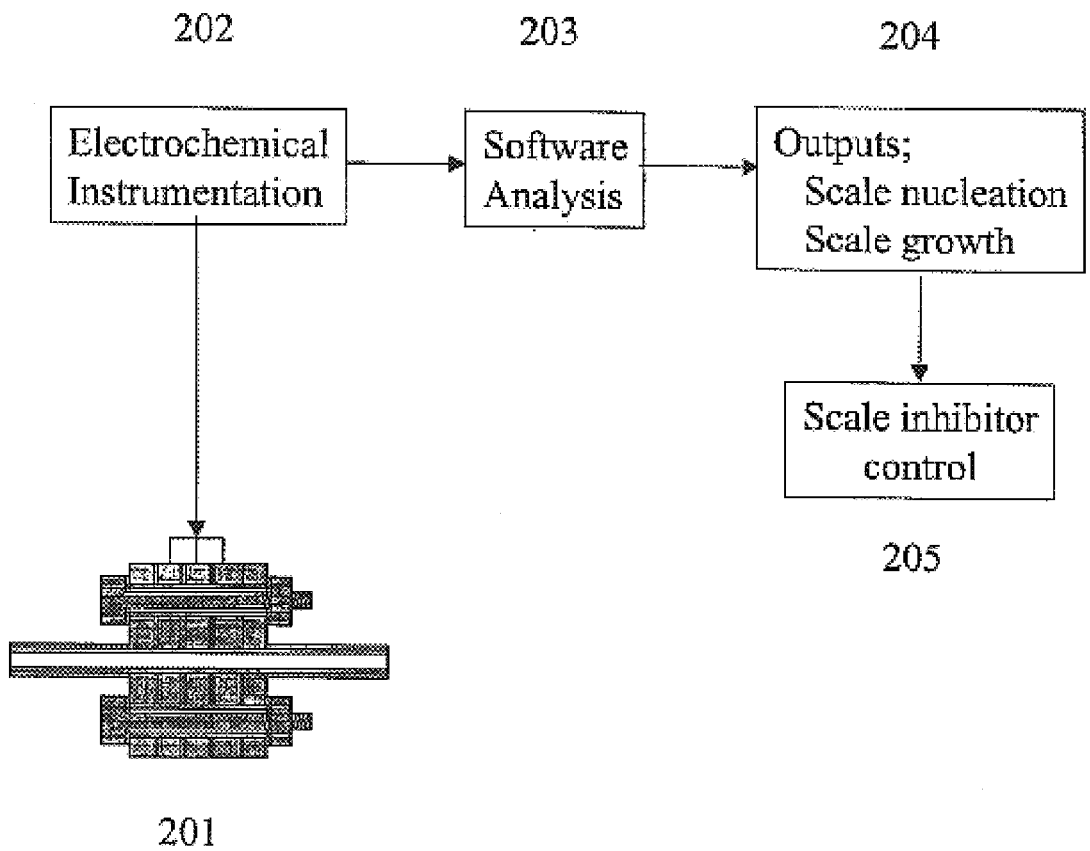
FIG. 2 is a schematic drawing of a sensor array in electrical communication with electrochemical instrumentation, software, control outputs, and scale inhibitor controls according to a farther aspect of the invention.

Referring now to FIG. 2, the sensor array housed in flanged sensor body 201 is connected in electrical communication to an electrochemical instrumentation package 202. The electrochemical responses generated by the sensors 101–103 responsive to scale nucleation and deposition are measured and analyzed by electrochemical instrumentation package 202, the outputs of package 202 are then further analyzed by software analyzer 203. Software analyzer 203 then sends an appropriate analysis signal to output controller 204, which sends a control output signal suitable for initiation of scale inhibitor control measures via scale inhibitor controller 205.

According to one aspect of the invention, when sensor array 101–103 is formed from a material selected for its high resistance to corrosion in a given application, those of ordinary skill in the art will appreciate that the electrochemical responses regarding scale formation that are generated by the sensor array will not be significantly compounded or amplified or distorted by corrosion-related effects, and thus any scale nucleation and deposition growth can be detected and monitored by electrochemical means. In a particularly preferred aspect of the invention, sensor array 101–103 will be formed from a material sufficiently resistant to corrosion given the application environment so as to permit a corrosion rate equal to or less than 0.01 mm per year (0.4 mils per year).

As mentioned, with respect to the detection of scale nucleation and deposition growth generally, it is important to minimize the effects of secondary processes, such as corrosion, within the sensor environment 201 that may adversely affect the accuracy of any electrochemical response signal transmitted to electrochemical instrumentation package 202 by the sensor. As a practical matter, the sensor material will be chosen for minimal corrosion characteristics relating to the scaling fluids of particular interest, for example, 316L stainless steel or the like for many common industrial applications.

Electrochemical scale nucleation and deposition processes will therefore occur at the highly energetic interface boundary of the stainless steel and the passing scaling fluid (the electrochemical double layer). The electrochemical double layer effectively constitutes an electrolytic capacitor, with a typical capacitance of between 10 and 100 microfarads per square centimeter. This capacitance is formed by adsorption of water molecules, dipoles, and ions in the electrochemical double layer at the metal/solution phase boundary.

When scale nucleation on the metal surface occurs, subtle variations in the double layer capacitance will occur as the ions adsorbed at the metal surface begin to form precipitates. These variations are observed as the characteristic responses in the electrochemical noise signals of both the current and potential signals.

In order to better characterize the electrochemical response, the analysis involves calculation of a number of factors relating to the signal distributions, in particular the Kurtosis and Skew of the potential and current signals, these factors being especially sensitive to the electrochemical changes occurring within the double layer.

As mentioned, the sensor optimally comprises three approximately identical electrodes of material known to have minimal corrosion in the scaling fluids of interest, for example 316L stainless steel. The electrodes 101–103 (referring again here to FIG. 1), which are kept electrically isolated from each other by gaskets 104–107, are continuously exposed to the produced fluids.

Electrochemical measurements of the responses of the electrodes to the fluid environment are made continuously by electrochemical instrumentation package 202, and will generally comprise one or more of the following types of measurements: electrochemical noise, linear polarization resistance, harmonic distortion analysis, intermodulation distortion analysis, solution resistance, and electrochemical impedance.

Electrochemical noise is a term of art used to describe the naturally occurring electrochemical current and potential signals. Potential noise refers to the spontaneous fluctuations in the open circuit potential of electrodes exposed to a fluid environment, and may be measured using a reference electrode to monitor changes in the sensing electrode;

alternatively, they may be measured between two sensing electrodes. Current noise refers to the fluctuations in the current observed by two identical sensing electrodes electrically coupled together with a zero-resistance ammeter or a similar device. Typically, electrochemical current and potential noise are measured simultaneously.

Linear polarization resistance is a measurement of the resistance of the electrochemical interface, typically made by imposing a small perturbation of around 10 to 30 millivolts to the sensing electrode(s). The current response is measured, and the resistance (i.e., the ratio of the applied voltage to the measured current) evaluated.

Harmonic distortion analysis involves applying a low frequency sinusoidal potential perturbation of a known frequency to the sensing electrode(s) and measuring the in-phase current response at the same frequency. Distortion occurs due to non-linearities in the electrochemical response, and is typically characterized by generation of harmonics at twice and three times the frequency of the applied signal.

Inter-modulation distortion analysis is similar to harmonic distortion analysis, with the applied signal being a composite of two sinusoids and the signal being analyzed for inter-modulation products.

Solution resistance is measured by applying a high frequency potential signal, for example, greater than 2 kilohertz, and then measuring the current response. The solution resistance is the ratio of the amplitude of the applied potential signal to the measured current response.

Electrochemical impedance characterizes the impedance of the sensor/electrolyte interface over a wide range of frequencies, typically between, for example, 10 millihertz and 20 kilohertz.

For purposes of detecting scale formation in the fluids of interest, it is important to have a continuous measurement, and an output of the scaling progress such that scale inhibitor treatments may be made in a timely and effective manner. In order to achieve this goal the instrumentation package 202 monitors the sensors 101–103 continuously using one or a combination of the techniques described above, but in particular a combination of electrochemical noise, linear polarization resistance, harmonic distortion analysis and solution resistance. The instrumentation package 202 provides data outputs, which relate to the scaling progress (in particular derivatives of the electrochemical noise measurements), with secondary outputs from the other electrochemical techniques.

Figure 3:
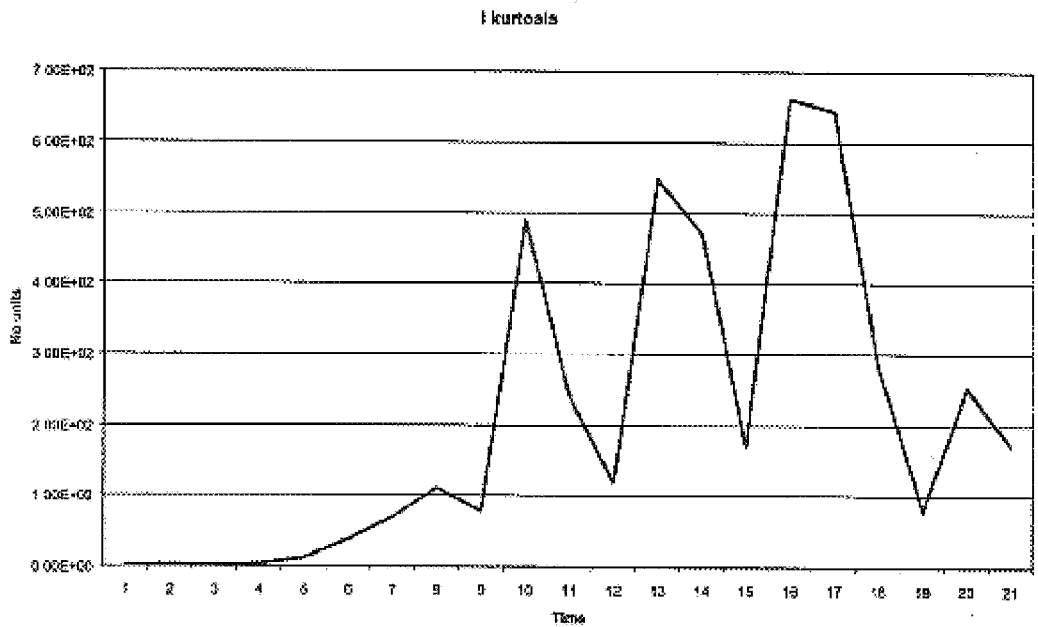
FIG. 3 is a graphical representation of a typical current noise signal analysis of the current Kurtosis during scale nucleation as a function of time according to a further aspect of the invention.

Referring now to FIG. 3, a graph illustrating a typical response of the current noise signal analysis of the current Kurtosis during scale nucleation is provided, showing sharp increases in the value as nucleation of the scale proceeds. Appropriate scaling fluid chemistries are shown below in Tables 1 and 2, where Table 1 illustrates a typical chemistry for a formation prone to carbonate scale formation, and Table 2 illustrates the compositions of the two water chemistries used for the tests, which, when mixed, would lead to carbonate scale formation within a period of around five minutes. The time scale for FIG. 3 is in minutes.

TABLE 1

| Ion | Formation (mg/L) |
|---|---|
| Na | 12,658 |
| Ca | 729 |

TABLE 1-continued

| Ion | Formation (mg/L) |
|---|---|
| Mg | 100 |
| K | 313 |
| Sr | 127 |
| Ba | 203 |
| Cl | 21,569 |
| $SO_4$ | 7 |
| $HCO_3$ | 591 |
| $CO_3$ | 0 |
| Fe | 0 |

TABLE 2

| Compound | 1 Liter Water (cations plus ½ NaCl) | 1 Liter Water (anions plus ½ NaCl) |
|---|---|---|
| $Na_2SO_4$ | | 0.0221 |
| $NaHCO_3$ | | 1.628 |
| NaCl | 32.137 | 32.137 |
| $CaCl_2.6H_2O$ | 7.97 | |
| $MgCl_2.6H_2O$ | 1.673 | |
| $BaCl_2.2H_2O$ | 0.722 | |
| $SrCl_2.6H_2O$ | 0.773 | |
| KCl | 1.194 | |
| Measured pH | 5.9 | 7.88 |

Figure 4:
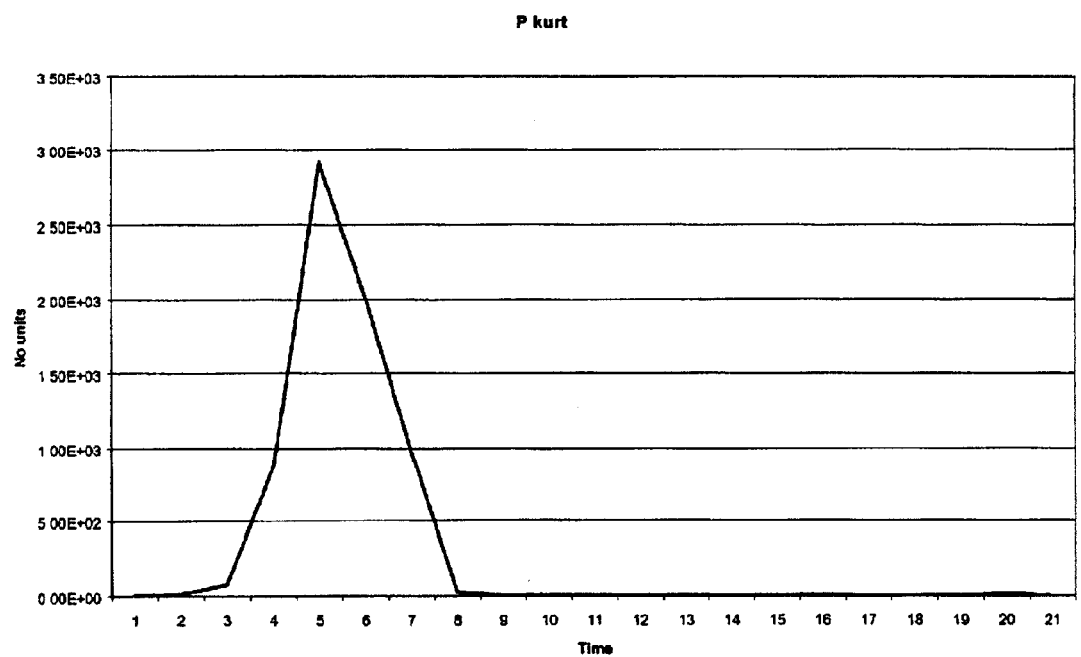
FIG. 4 is a graphical representation of a typical potential noise signal of the potential Kurtosis as a function of time according to a further aspect of the invention.

FIG. 4 illustrates the typical response of the potential noise signal of the potential Kurtosis over the same time period as the current noise analysis in FIG. 3, showing a sharp increase in value as nucleation of scale proceeds. Again, the time scale is in minutes.

Figure 5:
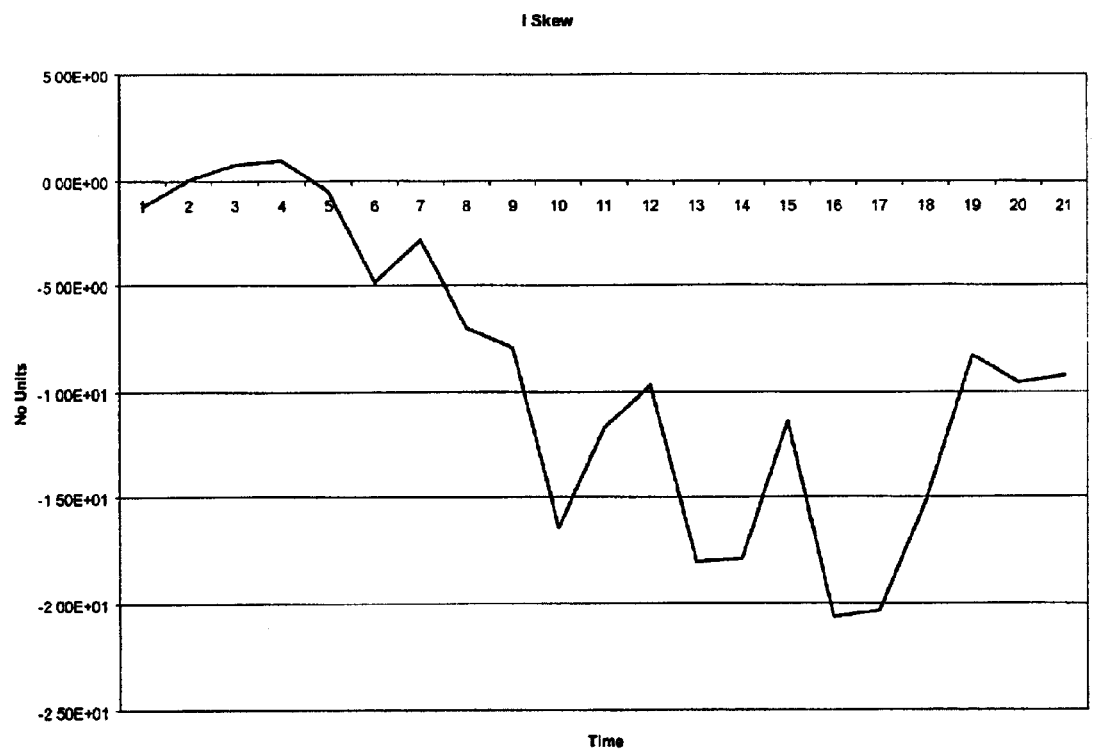
FIG. 5 is a graphical illustration of a typical current noise signal of the current Skew as a function of time according to a further aspect of the invention.

FIG. 5 illustrates the response of the current noise signal of the current Skew over the same time period as in FIG. 3, showing changes due to nucleation and growth of scale. The time scale is in minutes.

Figure 6:
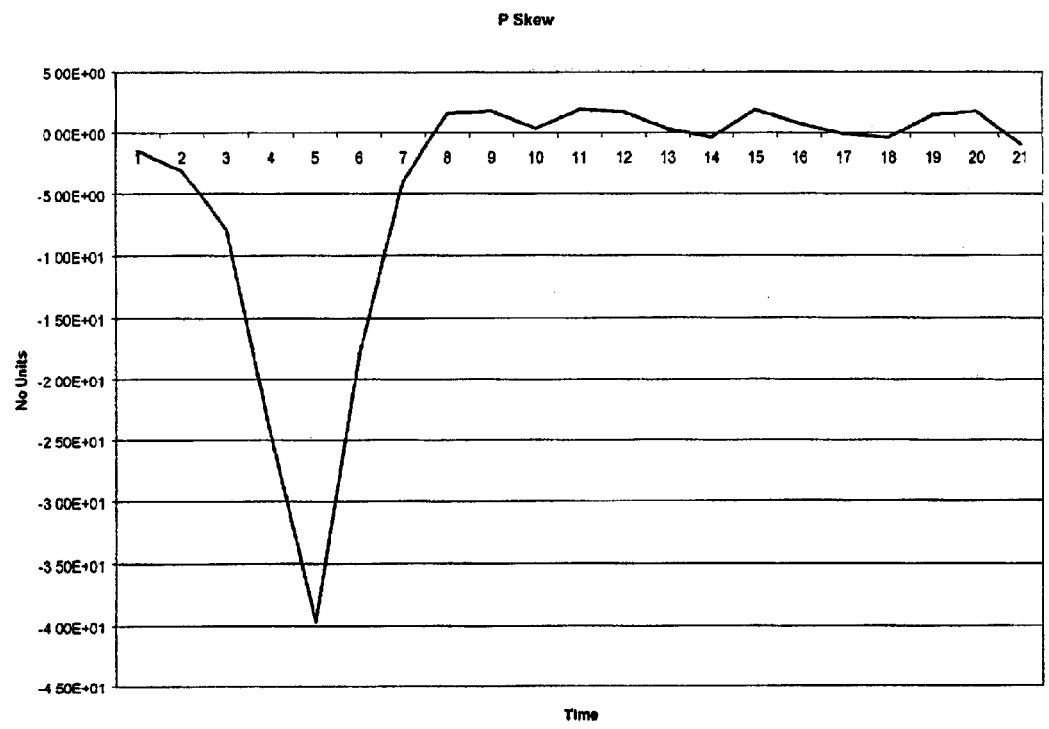
FIG. 6 is a graphical representation of a typical potential noise signal of the potential Skew as a function of time according to a further aspect of the invention.

FIG. 6 illustrates the typical response of the potential noise signal of the potential Skew over the same time period as in FIG. 3, showing changes due to nucleation of scale. Again, the time scale is in minutes.

Figure 7:
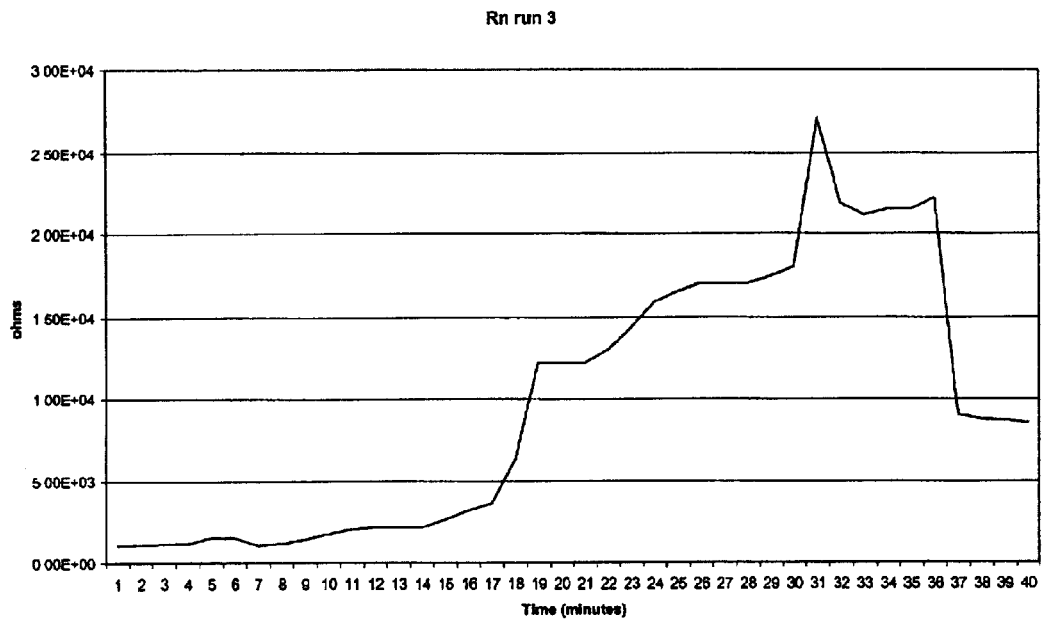
FIG. 7 is a graphical representation of a typical evolution of the electrochemical noise resistance during nucleation and growth as a function of time according to a further aspect of the invention.

FIG. 7 illustrates the evolution of the electrochemical noise resistance during nucleation and growth of scale over the same time period as in FIG. 3. The time scale is minutes.

Figure 8:
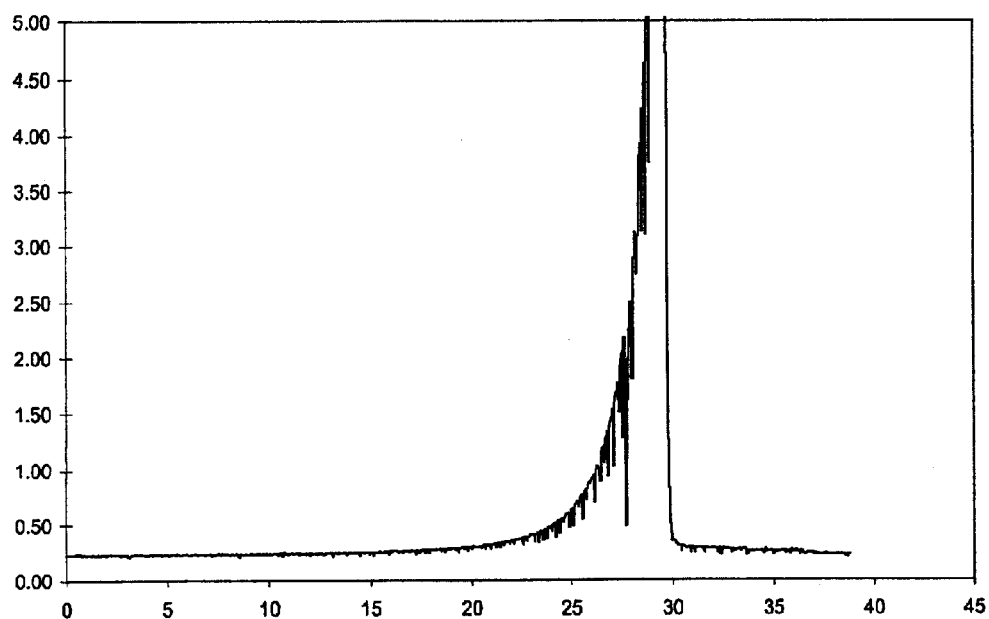
FIG. 8 is a graphical representation of a typical pressure drop experienced due to scale formation in a micro-bore tube according to a further aspect of the invention.

FIG. 8 illustrates the pressure drop experienced due to scale formation in micro-bore tube. Appropriate scaling fluid chemistries are shown immediately below in Tables 3 and 4, where Table 3 illustrates typical chemistries of formation and satellite waters, which, when mixed, will lead to formation of barium sulphate scales, and Table 4 illustrates the compositions of the two water chemistries used for the sulphate scaling tests. The time scale for FIG. 8 is also in minutes.

TABLE 3

| Ion | Formation (mg/L) | Satellite (mg/L) |
|---|---|---|
| Na | 25,591 | 10,890 |
| Ca | 500 | 428 |
| Mg | 91 | 1,368 |
| K | 1,100 | 460 |
| Sr | 60 | 7 |
| Ba | 650 | 0 |
| Cl | 42,000 | 19,800 |
| $SO_4$ | 0 | 2,850 |

TABLE 3-continued

| Ion | Formation (mg/L) | Satellite (mg/L) |
|---|---|---|
| $HCO_3$ | 2050 | 124 |
| $CO_3$ | 0 | 0 |
| Fe | 0 | 0 |

TABLE 4

| Compound | 1 Liter Water (cations plus ½ NaCl) | 1 Liter Water (anions plus ½ NaCl) |
|---|---|---|
| $Na_2SO_4$ | | 4.217 |
| $NaHCO_3$ | | 2.994 |
| NaCl | 44.587 | 44.587 |
| $CaCl_2.6H_2O$ | 5.073 | |
| $MgCl_2.6H_2O$ | 12.204 | |
| $BaCl_2.2H_2O$ | 1.156 | |
| $SrCl_2.6H_2O$ | 0.204 | |
| KCl | 2.975 | |

Figure 9:
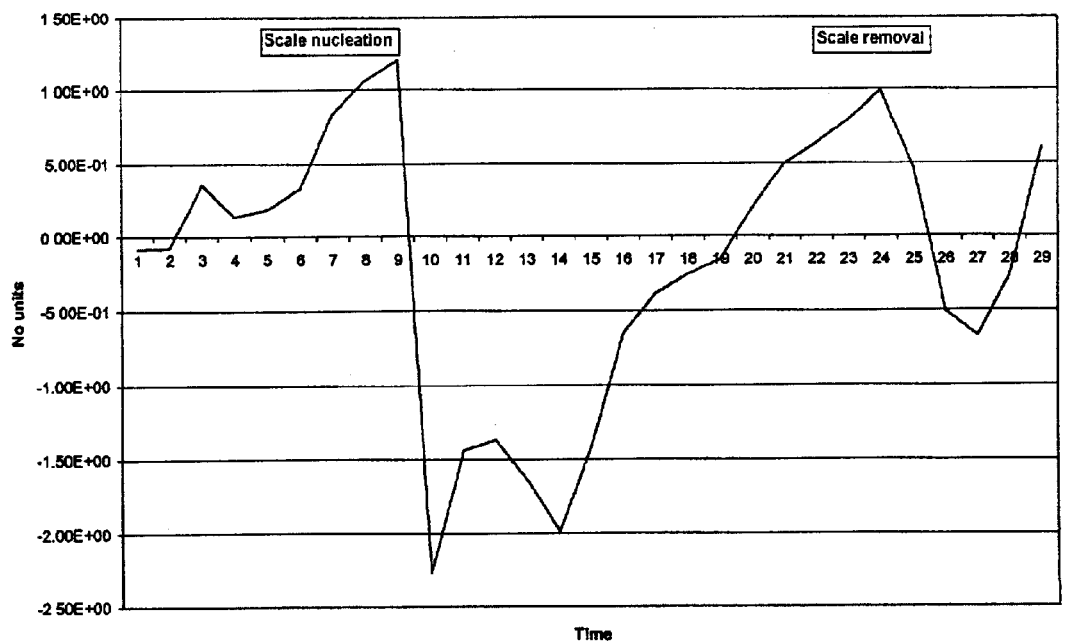
FIG. 9 is a graphical representation of a typical potential noise signal of the potential Skew during scale nucleation growth and removal as a function of time according to a further aspect of the invention.

FIG. 9 illustrates the typical response of the potential noise signal of the potential Skew during scale nucleation growth and removal over the same time period as in FIG. 8. The time scale is in minutes.

Figure 10:
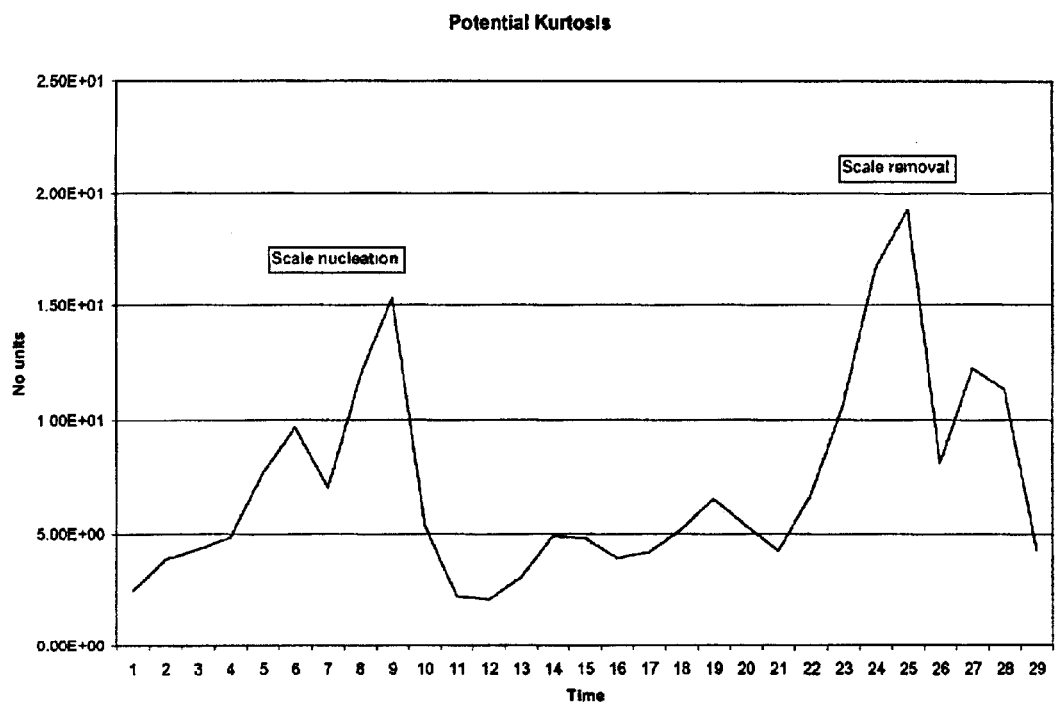
FIG. 10 is a graphical representation of a typical potential noise signal of the potential Kurtosis during scale nucleation growth and removal as a function of time according to a further aspect of the invention.

FIG. 10 illustrates the typical response of the potential noise signal of the potential Kurtosis during scale nucleation growth and removal over the same time period as in FIG. 8. The time scale is also in minutes.

Figure 11:
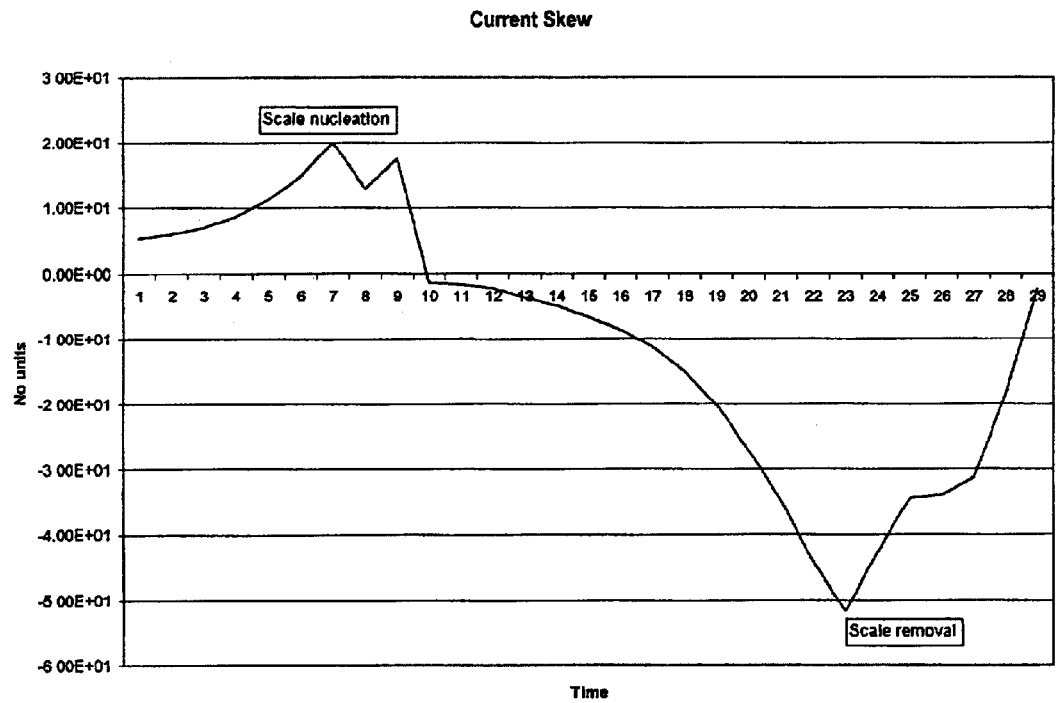
FIG. 11 is a graphical representation of a typical current noise signal of the current Skew during scale nucleation growth and removal as a function of time according to a further aspect of the invention.

FIG. 11 illustrates the typical response of the current noise signal of the current Skew during scale nucleation growth and removal over the same time period as in FIG. 8. The time scale is again in minutes.

Figure 12:
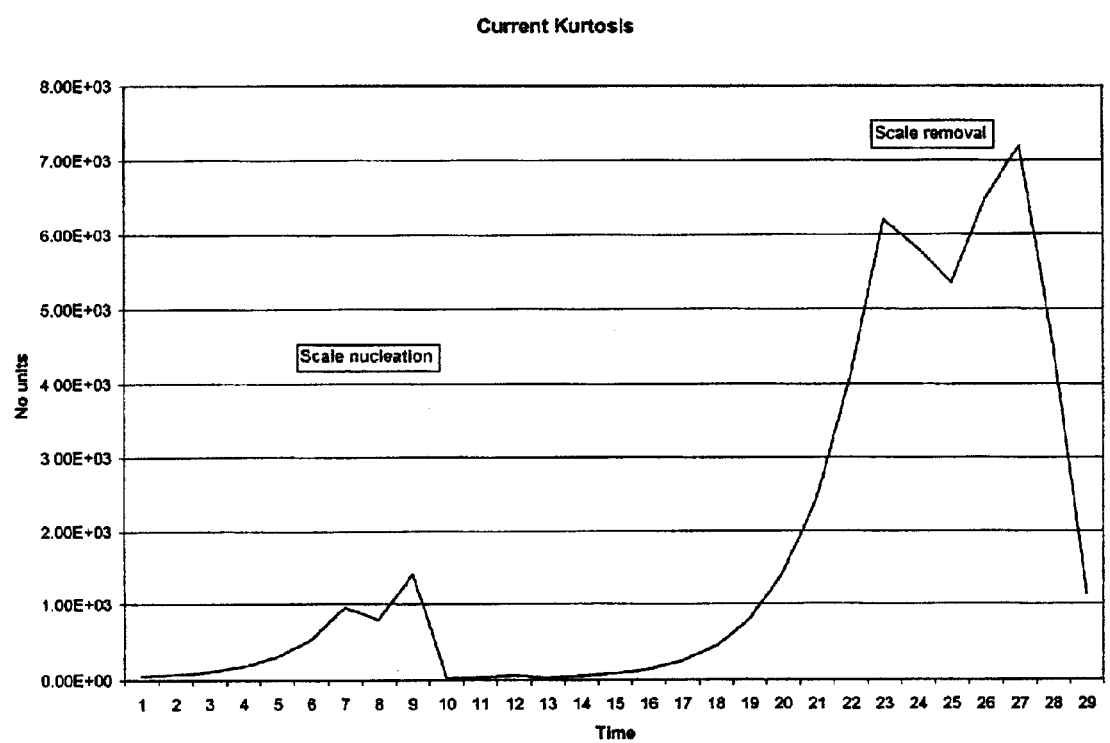
FIG. 12 is a graphical representation of a typical current noise signal of the current Kurtosis during scale nucleation growth and removal as a function of time according to a further aspect of the invention.

Finally, FIG. 12 illustrates the typical response of the current noise signal of the current Kurtosis during scale nucleation growth and removal over the same time period as in FIG. 8. The time scale is in minutes.

The foregoing specification is provided for illustrative purposes only, and is not intended to describe all possible aspects of the present invention. Moreover, while the invention has been shown and described in detail with respect to several exemplary embodiments, those of ordinary skill in the pertinent arts will appreciate that minor changes to the description, and various other modifications, omissions and additions may also be made without departing from either the spirit or scope thereof.

Having herein described the general nature and characteristics of the invention, what is claimed is:

1. An apparatus for electrochemical detection and control of inorganic scale, the apparatus comprising:
    a body member;
    a flow tube;
    a sensor array comprising a plurality of electrically isolated sections of electrochemically sensitive sensor material;
    a plurality of gasket sections that electrically isolate each of said sections of electrochemically sensitive sensor material, and
    an electrochemical instrumentation package that measures a plurality of electrochemical response signals generated by said sensor array when said sensor array detects the presence of one or more inorganic scale nucleation sites.

2. The apparatus for electrochemical detection and control of inorganic scale of claim 1, wherein said sensor array further comprises at least three electrically isolated sections of electrochemically sensitive sensor material.

3. The apparatus for electrochemical detection and control of inorganic scale of claim 1, wherein said sensor array further comprises less than three electrically isolated sections of electrochemically sensitive sensor material.

4. The apparatus for electrochemical detection and control of inorganic scale of claim 1, wherein said sensor array further comprises an electrochemically sensitive sensor material selected for its corrosion resistant properties.

5. The apparatus for electrochemical detection and control of inorganic scale of claim 1, wherein said sensor array further comprises an electrochemically sensitive sensor material sufficiently resistant to corrosion as to permit a corrosion rate of less than around 0.01 mm per year.

6. The apparatus for electrochemical detection and control of inorganic scale of claim 1, wherein said sensor array further comprises a stainless steel sensor material.

7. The apparatus for electrochemical detection and control of inorganic scale of claim 1, wherein said sensor array further comprises a 316L stainless steel sensor material.

8. The apparatus for electrochemical detection and control of inorganic scale of claim 1, wherein said plurality of gasket sections further comprises a dielectric insulating material.

9. The apparatus for electrochemical detection and control of inorganic scale of claim 1, wherein said plurality of gasket sections further comprises a PTFE material.

10. The apparatus for electrochemical detection and control of inorganic scale of claim 1, wherein said plurality of gasket sections further comprises a PVDF material.

11. The apparatus for electrochemical detection and control of inorganic scale of claim 1, wherein said electrochemical instrumentation package measures response signals generated by said sensor array when said sensor array detects the presence of one or more inorganic scale deposition sites.

12. The apparatus for electrochemical detection and control of inorganic scale of claim 1, wherein said electrochemical instrumentation package includes a set of outputs that output data regarding said measured electrochemical response signals to a set of inputs connected to a software analyzer, wherein said software analyzer analyzes said measured electrochemical response signals generated by said sensor array.

13. The apparatus for electrochemical detection and control of inorganic scale of claim 12, wherein said software analyzer further comprises a set of outputs that output control signals to an output controller, wherein said output controller initiates at least one inorganic scale inhibiting control measure using an inorganic scale inhibitor controller.

14. A method for electrochemically detecting and controlling inorganic scale, said method comprising:
    flowing a fluid through a flow tube so that said fluid flow is in fluid communication with a sensor array,
    wherein said sensor array comprises a set of outputs that output a plurality of electrochemical response signals to an electrochemical instrumentation package when said sensor array detects the presence of inorganic scale;
    measuring said plurality of electrochemical response signals generated by said sensor array using said electrochemical instrumentation package,
    wherein said electrochemical instrumentation package further comprises outputs that output data regarding said measured electrochemical response signals to a software analyzer;
    using said software analyzer to analyze said data regarding said measured electrochemical response signals and then outputting a plurality of control signals from said software analyzer to an output controller, and using said output controller to initiate at least one inorganic scale inhibiting control measure using an inorganic scale inhibitor controller.

15. The method of electrochemically detecting and controlling inorganic scale of claim 14, wherein said measuring said plurality of electrochemical response signals generated by said sensor array further consists of at least one measuring technique selected from the group including electrochemical noise, linear polarization resistance, harmonic distortion analysis, and solution resistance.

16. The method of electrochemically detecting and controlling inorganic scale of claim 14, wherein said measuring said plurality of electrochemical response signals further consists of at least one measuring technique selected from the group including electrochemical noise, linear polarization resistance, harmonic distortion analysis, solution resistance, inter-modulation distortion analysis, and electrical impedance.

17. A method for electrochemically detecting and controlling inorganic scale, the method comprising:

flowing a fluid through a flow tube so that said fluid flow remains in fluid communication with a sensor array, wherein said sensor array comprises a plurality of sections of electrochemically sensitive sensor material, and wherein said plurality of sections of electrochemically sensitive sensor material are electrically isolated from each other by means of plurality of gasket sections, and wherein said sensor array further comprises a set of electrodes for transmitting a plurality of electrochemical response signals generated by said sensor array's detection of inorganic scale to an electrochemical instrumentation package;

measuring said plurality of electrochemical response signals generated by said sensor array by means of said electrochemical instrumentation package, wherein said measuring said plurality of electrochemical response signals generated by said sensor array by means of said electrochemical instrumentation package further consists of at least one measuring technique selected from the group including electrochemical noise, linear polarization resistance, harmonic distortion analysis, solution resistance, inter-modulation distortion analysis, and electrical impedance, and wherein said electrochemical instrumentation package further comprises outputs for outputting data regarding said measured electrochemical response signals to a software analyzer; and analyzing said data regarding said measured electrochemical response signals by means of said software analyzer, wherein said software analyzer further comprises outputs for outputting a plurality of control signals to an output controller useful for initiating at least one inorganic scale inhibiting control measure by means of an inorganic scale inhibitor controller.

* * * * *